(12) United States Patent
Davidson et al.

(10) Patent No.: US 10,524,945 B2
(45) Date of Patent: Jan. 7, 2020

(54) STENTS TWISTED PRIOR TO DEPLOYMENT AND UNTWISTED DURING DEPLOYMENT

(71) Applicant: Covidien LP, Mansfield, MA (US)

(72) Inventors: James A. Davidson, San Juan Capistrano, CA (US); Masoud Molaei, Westminster, CO (US)

(73) Assignee: COVIDIEN LP, Mansfield, MA (US)

( * ) Notice: Subject to any disclaimer, the term of this patent is extended or adjusted under 35 U.S.C. 154(b) by 210 days.

(21) Appl. No.: 15/427,339

(22) Filed: Feb. 8, 2017

(65) Prior Publication Data

US 2017/0143522 A1 May 25, 2017

Related U.S. Application Data

(62) Division of application No. 14/136,297, filed on Dec. 20, 2013, now Pat. No. 9,592,139.

(Continued)

(51) Int. Cl.
*A61F 2/966* (2013.01)
*A61F 2/962* (2013.01)
(Continued)

(52) U.S. Cl.
CPC ............ *A61F 2/966* (2013.01); *A61F 2/90* (2013.01); *A61F 2/95* (2013.01); *A61F 2/962* (2013.01);
(Continued)

(58) Field of Classification Search
CPC ...... A61F 2/82; A61F 2/86; A61F 2/88; A61F 2/885; A61F 2/90; A61F 2/92; A61F 2/93; A61F 2/95; A61F 2/962; A61F 2/966; A61F 2/01; A61F 2/013; A61F 2/02; A61F 2/04; A61F 2/06; A61F 2/07; A61F 2/954; A61F 2/2418; A61F 2/243; A61F 2/2439; A61F 2/2463; A61F 2/2466; A61F 2002/011; A61F 2002/015; A61F 2002/016; A61F 2002/018; A61F 2002/061; A61F 2002/072; A61F 2002/075; A61F 2002/078; A61F 2002/823; A61F 2002/825;
(Continued)

(56) References Cited

U.S. PATENT DOCUMENTS 5,824,053 A * 10/1998 Khosravi .................. A61F 2/88
623/1.15
5,833,699 A * 11/1998 Chuter ...................... A61F 2/88
623/1.15

(Continued)

FOREIGN PATENT DOCUMENTS

EP 2319575 B1 11/2013
JP 2013066763 A 4/2013
(Continued)

*Primary Examiner* — Kathleen S Holwerda
*Assistant Examiner* — Kankindi Rwego
(74) *Attorney, Agent, or Firm* — Fortem IP LLP; Matthew Lincicum

(57) ABSTRACT

Stents can become twisted during deployment within tortuous vessels such that proper expansion against the vessel wall is inhibited. Stents can be twisted prior to deployment in a direction opposite the direction of twisting during deployment to facilitate full expansion of the stent against the vessel wall along the stent's entire length.

15 Claims, 7 Drawing Sheets

Related U.S. Application Data

(60) Provisional application No. 61/886,975, filed on Oct. 4, 2013.

(51) Int. Cl.
*A61F 2/90* (2013.01)
*A61F 2/95* (2013.01)

(52) U.S. Cl.
CPC ............ *A61F 2002/9505* (2013.01); *A61F 2210/0014* (2013.01); *A61F 2230/0091* (2013.01)

(58) Field of Classification Search
CPC .......... A61F 2002/826; A61F 2002/828; A61F 2002/9505; A61F 2002/9511; A61F 2002/9517; A61F 2002/9522; A61F 2002/9528; A61F 2002/9534; A61F 2002/9665
See application file for complete search history.

(56) References Cited

U.S. PATENT DOCUMENTS

| | | | |
|---|---|---|---|
| 5,948,017 A | 9/1999 | Taheri | |
| 6,123,723 A * | 9/2000 | Konya | A61F 2/07 606/108 |
| 6,974,473 B2 | 12/2005 | Barclay et al. | |
| 7,147,655 B2 | 12/2006 | Chermoni | |
| 7,771,463 B2 * | 8/2010 | Ton | A61F 2/88 623/1.11 |
| 7,785,361 B2 | 8/2010 | George et al. | |
| 8,603,014 B2 | 12/2013 | Alleman et al. | |
| 8,837,800 B1 | 9/2014 | Bammer et al. | |
| 9,119,656 B2 | 9/2015 | Bose et al. | |
| 9,126,018 B1 | 9/2015 | Garrison | |
| 9,211,132 B2 | 12/2015 | Bowman | |
| 9,241,699 B1 | 1/2016 | Kume et al. | |
| 9,265,512 B2 | 2/2016 | Garrison et al. | |
| 9,308,007 B2 | 4/2016 | Cully et al. | |
| 9,399,118 B2 | 7/2016 | Kume et al. | |
| 9,445,828 B2 | 9/2016 | Turjman et al. | |
| 9,445,829 B2 | 9/2016 | Brady et al. | |
| 9,492,637 B2 | 11/2016 | Garrison et al. | |
| 9,539,022 B2 | 1/2017 | Bowman | |
| 9,561,345 B2 | 2/2017 | Garrison et al. | |
| 9,579,119 B2 | 2/2017 | Cully et al. | |
| 9,585,741 B2 | 3/2017 | Ma | |
| 9,592,139 B2 | 3/2017 | Davidson et al. | |
| 9,642,635 B2 | 5/2017 | Vale et al. | |
| 9,655,633 B2 | 5/2017 | Leynov et al. | |
| 9,737,318 B2 | 8/2017 | Monstadt et al. | |
| 9,770,251 B2 | 9/2017 | Bowman et al. | |
| 9,801,643 B2 | 10/2017 | Hansen et al. | |
| 9,861,783 B2 | 1/2018 | Garrison et al. | |
| 9,993,257 B2 | 6/2018 | Losordo et al. | |
| 10,028,782 B2 | 7/2018 | Orion | |
| 10,029,008 B2 | 7/2018 | Creighton | |
| 10,039,906 B2 | 8/2018 | Kume et al. | |
| 2003/0135266 A1 * | 7/2003 | Chew | A61F 2/91 623/1.16 |
| 2003/0187497 A1 | 10/2003 | Boylan et al. | |
| 2003/0191528 A1 | 10/2003 | Quijano et al. | |
| 2006/0079955 A1 * | 4/2006 | Brown | A61F 2/88 623/1.22 |
| 2006/0111771 A1 | 5/2006 | Ton et al. | |
| 2006/0184232 A1 | 8/2006 | Gianotti et al. | |
| 2007/0055299 A1 * | 3/2007 | Ishimaru | A61F 2/07 606/191 |
| 2008/0114445 A1 | 5/2008 | Melsheimer et al. | |
| 2008/0125849 A1 | 5/2008 | Burpee et al. | |
| 2008/0249457 A1 | 10/2008 | Li et al. | |
| 2008/0255655 A1 | 10/2008 | Kusleika et al. | |
| 2008/0294267 A1 | 11/2008 | Chanduszko et al. | |
| 2011/0238041 A1 | 9/2011 | Lim et al. | |
| 2012/0109280 A1 | 5/2012 | McHugo et al. | |
| 2012/0165921 A1 | 6/2012 | Casey et al. | |
| 2012/0296408 A1 * | 11/2012 | Jones | A61B 17/12 623/1.11 |
| 2013/0030461 A1 | 1/2013 | Marks et al. | |
| 2013/0281788 A1 | 10/2013 | Garrison | |
| 2014/0276074 A1 | 9/2014 | Warner | |
| 2014/0343595 A1 | 11/2014 | Monstadt et al. | |
| 2015/0359547 A1 | 12/2015 | Vale et al. | |
| 2016/0015402 A1 | 1/2016 | Brady et al. | |
| 2016/0015935 A1 | 1/2016 | Chan et al. | |
| 2016/0106448 A1 | 4/2016 | Brady et al. | |
| 2016/0106449 A1 | 4/2016 | Brady et al. | |
| 2016/0113663 A1 | 4/2016 | Brady et al. | |
| 2016/0113665 A1 | 4/2016 | Brady et al. | |
| 2016/0151618 A1 | 6/2016 | Powers et al. | |
| 2016/0157985 A1 | 6/2016 | Vo et al. | |
| 2016/0199620 A1 | 7/2016 | Pokorney et al. | |
| 2016/0296690 A1 | 10/2016 | Kume et al. | |
| 2016/0302808 A1 | 10/2016 | Loganathan et al. | |
| 2016/0375180 A1 | 12/2016 | Anzai | |
| 2017/0079766 A1 | 3/2017 | Wang et al. | |
| 2017/0079767 A1 | 3/2017 | Leon-Yip | |
| 2017/0086862 A1 | 3/2017 | Vale et al. | |
| 2017/0100143 A1 | 4/2017 | Grandfield | |
| 2017/0105743 A1 | 4/2017 | Vale et al. | |
| 2017/0164963 A1 | 6/2017 | Goyal | |
| 2017/0215902 A1 | 8/2017 | Leynov et al. | |
| 2017/0224953 A1 | 8/2017 | Tran et al. | |
| 2017/0281909 A1 | 10/2017 | Northrop et al. | |
| 2017/0290599 A1 | 10/2017 | Youn et al. | |
| 2018/0049762 A1 | 2/2018 | Seip et al. | |
| 2018/0084982 A1 | 3/2018 | Yamashita et al. | |
| 2018/0116717 A1 | 5/2018 | Taff et al. | |
| 2018/0132876 A1 | 5/2018 | Zaidat | |
| 2018/0140314 A1 | 5/2018 | Goyal et al. | |
| 2018/0140315 A1 | 5/2018 | Bowman et al. | |
| 2018/0140354 A1 | 5/2018 | Lam et al. | |
| 2018/0185614 A1 | 7/2018 | Garrison et al. | |

FOREIGN PATENT DOCUMENTS

| | | |
|---|---|---|
| JP | 2014004219 A | 1/2014 |
| JP | 2018118132 A | 8/2018 |
| KR | 20180102877 A | 9/2018 |
| WO | 03020174 A1 | 3/2003 |
| WO | 2015141317 A1 | 9/2015 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 2018187776 A1 | 10/2018 |

* cited by examiner

STENTS TWISTED PRIOR TO DEPLOYMENT AND UNTWISTED DURING DEPLOYMENT

CROSS-REFERENCE TO RELATED APPLICATIONS

This application is a divisional of U.S. patent application Ser. No. 14/136,297, filed Dec. 20, 2013, titled STENTS TWISTED PRIOR TO DEPLOYMENT AND UNTWISTED DURING DEPLOYMENT, which claims the priority benefit of U.S. Provisional Patent Application No. 61/886,975, filed Oct. 4, 2013, titled STENTS TWISTED PRIOR TO DEPLOYMENT AND UNTWISTED DURING DEPLOYMENT, the entirety of both application are incorporated by reference herein.

BACKGROUND

Walls of the vasculature, particularly arterial walls, may develop areas of pathological dilatation called aneurysms. As is well known, aneurysms have thin, weak walls that are prone to rupturing. Aneurysms can be the result of the vessel wall being weakened by disease, injury, or a congenital abnormality. Aneurysms could be found in different parts of the body, and the most common are abdominal aortic aneurysms and brain or cerebral aneurysms in the neurovasculature. When the weakened wall of an aneurysm ruptures, it can result in death, especially if it is a cerebral aneurysm that ruptures.

Aneurysms are generally treated by excluding the weakened part of the vessel from the arterial circulation. For treating a cerebral aneurysm, such reinforcement is done in many ways including: (i) surgical clipping, where a metal clip is secured around the base of the aneurysm; (ii) packing the aneurysm with small, flexible wire coils (micro-coils); (iii) using embolic materials to "fill" an aneurysm; (iv) using detachable balloons or coils to occlude the parent vessel that supplies the aneurysm; and (v) intravascular stenting.

Intravascular stents are well known in the medical arts for the treatment of vascular stenoses or aneurysms. Stents are prostheses that expand radially or otherwise within a vessel or lumen to provide support against the collapse of the vessel. Various methods for delivering these intravascular stents are also known.

Blood vessels can become occluded by emboli, e.g., thrombi. For example, intracranial arteries can become occluded by thromboembolisms. Disruption of blood flow by the occlusion can prevent oxygen and nutrients from being delivered to tissues downstream of the occlusion. Deprivation of oxygen and nutrients to tissue distal to an occlusion can impair proper function of the tissue, and may result in cellular death. Cellular death increases with duration of the occlusion. Stent-like mechanical thrombectomy devices have been used to revascularize and/or remove occlusive thrombi.

SUMMARY

The curvature of a blood vessel within which a stent is being delivered can result in rotation of the stent-delivery catheter as it is moved through the blood vessel. As the stent is deployed by withdrawing the catheter over the stent, a twisting action on the catheter due to the vessel curvature can impose a torque force to the stent. A moment induced by that torque force on the stent can cause some stents, particularly longer ones, not to expand fully during delivery (e.g., develop a "kink"). When a stent becomes kinked during deployment, the physician is often required to manipulate the catheter or delivery wire to relieve the torque on the stent, or insert a balloon after deployment to open up the kinked region of the deployed stent. Both options are tedious and may not resolve the kink.

An aspect of at least some of the embodiments disclosed herein involves the recognition that pretwisting a stent can counteract the twisting imposed on the stent during delivery into tortuous vessels. For example, before delivery, a stent can be twisted in a rotational direction opposite the expected direction of catheter rotation during delivery. In some embodiments, pretwisting a stent can counteract, and possibly eliminate, the twisting effect and kinking tendency of the stent during delivery, especially in more severely curved blood vessels. In some embodiments, pretwisting a stent to a sufficient extent can reduce the braid angle and overall stent diameter to allow the stent to be pushed with less delivery force.

Long diverter devices can be difficult or impossible to advance through a catheter due to higher friction forces between the stent and an interior surface of the catheter. Thus, in some instances, multiple shorter stents must be used instead of a preferred longer stent. An aspect of at least some of the embodiments disclosed herein involves the recognition that longer stents can be delivered by preloading a stent into a delivery catheter and delivering the preloaded catheter through a larger catheter, over a guide wire, or both to its intended position in the vessel. In some embodiments, the stent can be prepositioned at or near a distal tip of the delivery catheter. In some embodiments, the delivery catheter can contain a pusher located proximal to the stent to hold the stent in place while the delivery catheter is retracted during deployment of the stent.

The subject technology is illustrated, for example, according to various aspects described below. Various examples of aspects of the subject technology are described as numbered embodiments (1, 2, 3, etc.) for convenience. These are provided as examples and do not limit the subject technology. It is noted that any of the dependent embodiments may be combined in any combination, and placed into a respective independent embodiments, to form an independent embodiments. The other embodiments can be presented in a similar manner. The following is a non-limiting summary of some embodiments presented herein.

Embodiment 1. A method for placing a stent within an intracranial vessel, the method comprising:
   (a) providing a stent comprising a first end, a second end, and a tubular, mesh wall between the first end and the second end, the mesh wall being contiguous in circumferential and longitudinal directions from the first end to the second end, the stent having a rest configuration in the absence of external forces, and a twisted configuration in which the stent is (i) collapsed toward a longitudinal axis of the stent from the rest configuration and (ii) twisted about the longitudinal axis from the rest configuration;
   (b) advancing the stent into the intracranial vessel while holding the stent in the twisted configuration;
   (c) expanding the first end of the stent against a wall of the intracranial vessel;
   (d), after (c), untwisting the stent while expanding portions of the mesh wall of the stent progressively farther from the first end; and
   (e) expanding the second end of the stent against the wall of the intracranial vessel.

Embodiment 2. The method of Embodiment 1, wherein the stent is configured for self-expansion, and (b) comprises advancing the stent through a catheter, (c) comprises retracting a distal end of the catheter to expose the first end of the stent to expand the first end of the stent, and (d) comprises retracting the distal end of the catheter toward the second end of the stent while rotating the distal end of the catheter.

Embodiment 3. The method of Embodiment 2, wherein the distal end of the catheter is rotated while retracting a proximal end of the catheter without significant rotation of the proximal end of the catheter.

Embodiment 4. The method of Embodiment 2, wherein the distal end of the catheter is rotated at least 180 degrees about a longitudinal axis of the catheter from (c) to (e) while rotating the proximal end of the catheter less than 180 degrees.

Embodiment 5. The method of Embodiment 2, wherein the distal end of the catheter is rotated at least 360 degrees about a longitudinal axis of the catheter from (c) to (e) while rotating the proximal end of the catheter less than 180 degrees.

Embodiment 6. The method of Embodiment 1, wherein the stent is advanced into the intracranial vessel while the stent is twisted more than is necessary to collapse the stent.

Embodiment 7. The method of Embodiment 6, wherein the stent is only partially untwisted from (c) to (e).

Embodiment 8. The method of Embodiment 1, wherein the stent has a length of at least 50 mm, and the stent is expanded within the intracranial vessel without a kink.

Embodiment 9. The method of Embodiment 8, wherein the stent is expanded within the intracranial vessel such that a minimum transverse inside dimension of the stent is at least 50% of a maximum transverse inside dimension of the stent.

Embodiment 10The method of Embodiment 8, wherein an entire circumference of the stent along an entire length of the mesh wall of the stent is expanded into contact with the wall of the intracranial vessel.

Embodiment 11. A stent comprising a first end, a second end, and a tubular, mesh wall between the first end and the second end, the mesh wall being contiguous in circumferential and longitudinal directions from the first end to the second end, the stent having a rest configuration in the absence of external forces, and a twisted configuration in which the stent is (i) collapsed toward a longitudinal axis of the stent from the rest configuration and (ii) twisted about the longitudinal axis from the rest configuration, wherein the stent is in the twisted configuration.

Embodiment 12. The stent of Embodiment 11, wherein, in the twisted configuration, the first end of the stent is rotated, about the longitudinal axis, by at least 180 degrees relative to the second end of the stent in the rest configuration.

Embodiment 13. The stent of Embodiment 12, wherein, in the twisted configuration, the first end of the stent is rotated, about the longitudinal axis, by at least 360 degrees relative to the second end of the stent in the rest configuration.

Embodiment 14. The stent of Embodiment 11, wherein, in the twisted configuration, the first end of the stent is rotated, about the longitudinal axis, relative to the second end more than is necessary to collapse the stent for positioning the stent in the sheath.

Embodiment 15. The stent of Embodiment 11, wherein the stent has a length of at least 50 mm.

Embodiment 16. The stent of Embodiment 11, wherein the stent comprises a plurality of braided filaments.

Embodiment 17. A stent assembly, comprising a sheath and the stent of Embodiment 11, wherein the stent is held in the sheath in the twisted configuration.

Embodiment 18. A kit, comprising:
  a plurality of stents, each stent of the plurality of stents comprising first end, a second end, and a tubular, mesh wall between the first end and the second end, the mesh wall being contiguous in circumferential and longitudinal directions from the first end to the second end, each stent having a rest configuration in the absence of external forces, and a twisted configuration in which the stent is (i) collapsed toward a longitudinal axis of the stent from the rest configuration and (ii) twisted about the longitudinal axis from the rest configuration;
  wherein a first stent of the plurality of stents is in the twisted configuration, and is twisted in a first rotational direction about the longitudinal axis from its rest configuration; and
  wherein a second stent of the plurality of stents is in the twisted configuration, and is twisted in a second rotational direction, opposite the first rotation direction, about the longitudinal axis from its rest configuration.

Embodiment 19. The kit of Embodiment 18, wherein, in the twisted configuration of each stent of the plurality of stents, the first end is rotated, about the longitudinal axis, by at least 180 degrees relative to the second end in the rest configuration.

Embodiment 20. The kit of Embodiment 19, wherein, in the twisted configuration of each stent of the plurality of stents, the first end is rotated, about the longitudinal axis, by at least 360 degrees relative to the second end in the rest configuration.

Embodiment 21. The kit of Embodiment 19, wherein at least some of the stents are in the twisted configuration and are twisted by at least 720 degrees relative to the rest configuration, and at least some of the stents are in the twisted configuration and are twisted by less than 720 degrees relative to the rest configuration.

Embodiment 22. The kit of Embodiment 18, wherein, in the twisted configuration of each stent of the plurality of stents, the first end is rotated, about the longitudinal axis, relative to the second end more than is necessary to collapse the stent for positioning the stent in the sheath.

Embodiment 23. The kit of Embodiment 18, wherein at least some of the stents have a length of 50 mm to 70 mm, and at least some of the stents have a length of greater than 70 mm.

Embodiment 24. The kit of Embodiment 18, wherein each stent of the plurality of stents comprises a plurality of braided filaments.

Embodiment 25. The kit of Embodiment 18, wherein each stent of the plurality of stents is held in a sheath in the twisted configuration.

Embodiment 26. A method of treating a patient having an neurovascular condition, comprising:
  providing a plurality of stents, each stent of the plurality of stents comprising first end, a second end, the stent having a rest configuration in the absence of external forces, and a twisted configuration in which the stent is (i) collapsed toward a longitudinal axis of the stent from the rest configuration and (ii) twisted about the longitudinal axis from the rest configuration, each stent held in the twisted configuration;
  identifying a location for placement of a stent within the patient's neurovasculature;
  selecting, based on the location for placement and from among the plurality of stents, a stent for placement in the patient's neurovasculature, that is (a) twisted in a first rotational direction about the longitudinal axis, or (b) twisted in a second rotational direction, opposite the first rotation direction;

placing the selected stent in the neurovasculature; and expanding the selected stent within the neurovasculature.

Embodiment 27. The method of Embodiment 26, wherein the plurality of stents comprises stents of various nominal amounts of twist, and wherein the selected stent is selected, based on the neurovasculature at the location of placement, to have one of the various nominal amounts of twist.

Embodiment 28. The method of Embodiment 26, wherein the plurality of stents comprises stents of various nominal lengths, and wherein the selected stent is selected, based on the neurovasculature at the location of placement, to have one of the various lengths.

Embodiment 29. The method of Embodiment 26, wherein the plurality of stents comprises stents of various nominal transverse dimensions, and wherein the selected stent is selected, based on the neurovasculature at the location of placement, to have one of the various nominal transverse dimensions.

Embodiment 30. The method of Embodiment 26, wherein the stent is configured for self-expansion, and (b) comprises advancing the stent through a catheter, (c) comprises retracting a distal end of the catheter to expose the first end of the stent to expand the first end of the stent, and (d) comprises retracting the distal end of the catheter toward the second end of the stent while rotating the distal end of the catheter.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

Figure 1:
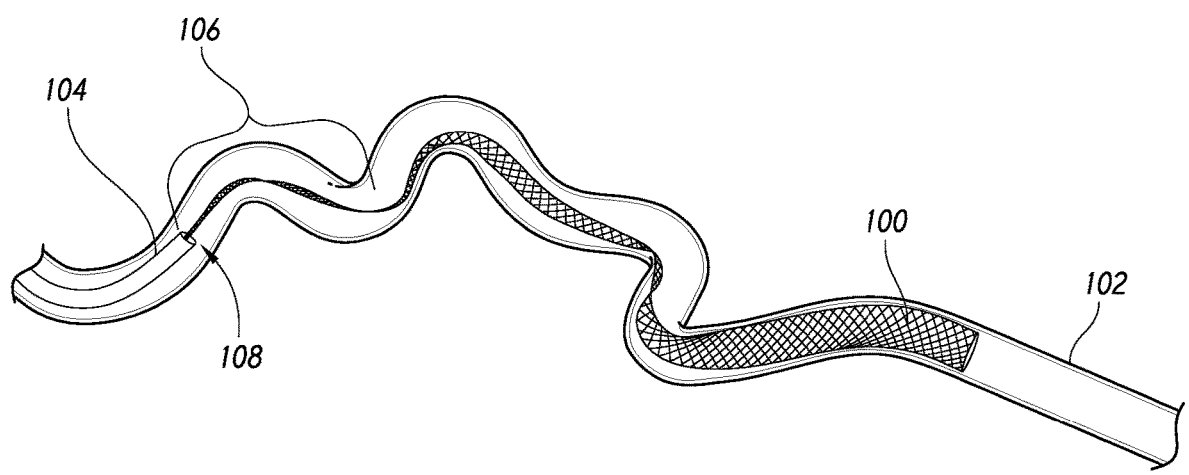
FIG. 1 illustrates deployment of a stent within a tortuous vessel, the stent being kinked, and a delivery catheter retracted proximally of the kinked segment of the stent.

The detailed description set forth below is intended as a description of various configurations of the subject technology and is not intended to represent the only configurations in which the subject technology may be practiced. The detailed description includes specific details for the purpose of providing a thorough understanding of the subject technology. However, the subject technology may be practiced without these specific details. In some instances, well-known structures and components are not shown, or are shown schematically or in block diagram form, to avoid obscuring the concepts of the subject technology.

Various embodiments of systems and methods for delivering stents are disclosed. Some of the embodiments have particular advantage in the expansion of long stents, e.g., having a length of 50 mm or greater. Various other features and advantages of embodiments are discussed in shown herein.

In some embodiments, a stent delivery system is provided that can include a stent, a pusher, and an introducer sheath and/or delivery catheter. The pusher can be movable within the introducer sheath and/or catheter to deliver the stent to a predetermined treatment site, such as at an aneurysm, within the vasculature of a patient. Thus, prior to delivery of the stent, the catheter can be configured to be introduced and advanced through the vasculature of the patient. The catheter can be made from various thermoplastics, e.g., polytetrafluoroethylene (PTFE or TEFLON®), fluorinated ethylene propylene (FEP), high-density polyethylene (HDPE), polyether ether ketone (PEEK), etc., which can optionally be lined on the inner surface of the catheter or an adjacent surface with a hydrophilic material such as polyvinylpyrrolidone (PVP) or some other plastic coating. Additionally, either surface can be coated with various combinations of different materials, depending upon the desired results.

The stent can take the form of a vascular occluding device, a revascularization device and/or an embolization device. In some embodiments, the stent can be an expandable stent made of two or more filaments. In some embodiments, the stent can be braided, woven, or cut from a sheet or tube. The filaments can be formed of known flexible materials including shape memory materials, such as nitinol, platinum and stainless steel. In some embodiments, the filaments can be round or ovoid wire. Further, the filaments can be configured such that the stent is self-expanding. In some embodiments, the stent can be fabricated from platinum/8% tungsten and 35N LT (cobalt nickel alloy, which is a low titanium version of MP35N alloy) alloy wires. In other embodiments, one or more of the filaments can be formed of a biocompatible metal material or a biocompatible polymer.

The wire filaments can be braided into a resulting lattice-like structure. In at least one embodiment, during braiding or winding of the stent, the filaments can be braided using a 1-over-2-under-2 pattern. In other embodiments, however, other methods of braiding can be followed, without departing from the scope of the disclosure. The stent can exhibit a porosity configured to reduce haemodynamic flow into and/or induce thrombosis within, for example, an aneurysm, but simultaneously allow perfusion to an adjacent branch vessel whose ostium is crossed by a portion of the stent. As will be appreciated, the porosity of the stent can be adjusted by "packing" the stent during deployment, as known in the art. The ends of the stent can be cut to length and therefore remain free for radial expansion and contraction. The stent can exhibit a high degree of flexibility due to the materials used, the density (i.e., the porosity) of the filaments, and the fact that the ends are not secured.

Information regarding additional embodiments, features, and other details of the occlusion devices or stents, methods of use, and other components that can optionally be used or implemented in embodiments of the occlusion devices or stents described herein, can be found in U.S. Pat. No. 8,409,269, issued on Apr. 2, 2013; U.S. Pat. No. 8,273,101, issued on Sep. 25, 2012; U.S. Pat. No. 8,398,701, issued on Mar. 19, 2013; Ser. No. 11/420,025, filed May 24, 2006; U.S. Patent Application Publication No. 2006/0206201, published on Sep. 14, 2006; U.S. Patent Application Publication No. 2009/0287288, published on Nov. 19, 2009; U.S. Patent Application Publication No. 2012/0083868, published on Apr. 5, 2012; U.S. patent application Ser. No. 13/795,556, entitled Methods and Apparatus for Luminal Stenting, filed on Mar. 12, 2013, now U.S. Pat. No. 9,295,571; U.S. Patent Application Publication No. 2013/0226276, published on Aug. 29, 2013; U.S. Patent Application Publication No. 2013/0226278, published on Aug. 29, 2013; U.S. patent application Ser. No. 13/664,547, entitled Methods and Apparatus for Luminal Stenting, filed on Oct. 31, 2012, published as U.S. Patent Application Publication No. 2013/0304185 on Nov. 14, 2013; U.S. Pat. No. 7,300,458, entitled Medical Implant Having a Curable Matrix Structure, issued Nov. 27, 2007; U.S. Patent Application Publication No. 2011/0060212, entitled Methods and Apparatus for Flow Restoration, published on Mar. 10, 2011; U.S. Patent Application Publication No. 2012/0083868, entitled Methods and Apparatuses for Flow Restoration and Implanting Members in the Human Body, published on Apr. 5, 2012; U.S. Patent Application Publication No. 2011/0160763, entitled Blood Flow Restoration in Thrombus Management Methods, published on Jun. 30, 2011; the entireties of each of which are incorporated herein by reference.

As discussed above, the curvature of a blood vessel within which a stent is being delivered can result a stent not fully expanding or developing a kink during delivery. FIG. 1 illustrates a stent 100 positioned within a tortuous vessel 102 during deployment of the stent. A delivery catheter 104 has been retracted proximally permit the stent 100, which is self-expanding in this instance, to expand against an inner wall of the vessel 102. However, as the catheter 104 was retracted, the distal end of the catheter rotated about a longitudinal axis of the catheter causing the stent to twist. This twisting of the stent impaired expansion of a segment 106, which became kinked and unable to expand despite retraction of the catheter.

In some embodiments, pretwisting a stent can counteract the twisting imposed on the stent during delivery into tortuous vessels, such as the vessel 102 illustrated in FIG. 1. Before delivery, the stent 100 can be twisted in a rotational direction opposite the expected direction of catheter rotation during delivery. The direction of twisting can be determined with reference to an end-on view of either end of the stent. The stent can be twisted by (i) rotating one end of the stent while inhibiting of preventing rotation of the other end, (ii) rotating both ends of the stent in opposite directions, (iii) rotating the ends of the stent in the same direction at different rates, or a combination of any of (i)-(iii).

Figure 3:
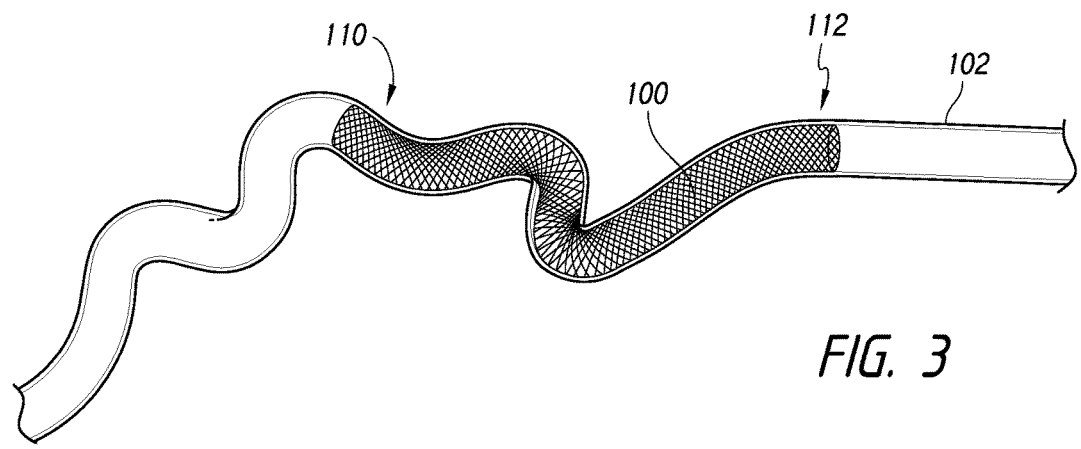
FIG. 3 illustrates a stent deployed within the tortuous vessel of FIG. 1, and the stent being fully deployed without a kink.

Consider, for example, a distal end 108 of the catheter rotates counterclockwise from an operators perspective at a proximal end (not shown) of the catheter. (This rotation would appear clockwise when viewing the distal end of the catheter from a location distal to the distal end of the catheter.) As the delivery catheter 104 is retracted, a proximal end 110 of the stent 100 will be rotated counterclockwise relative to a distal end 112 of the stent (see FIG. 3). In some embodiments, pretwisting the stent 100 in a clockwise direction, as indicated by arrows 116, about a longitudinal axis 114 can counteract, and possibly eliminate, the twisting effect of the counterclockwise rotation of the distal end of the catheter during retraction. FIG. 3 illustrates a stent 100 that was twisted three revolutions clockwise prior to deployment in the vessel 102. During deployment of the stent 100 illustrated in FIG. 3, the distal end of the catheter rotated counterclockwise, thereby untwisting the stent 100 during deployment such that the stent numeral 100 deployed without a kink.

Figure 4:
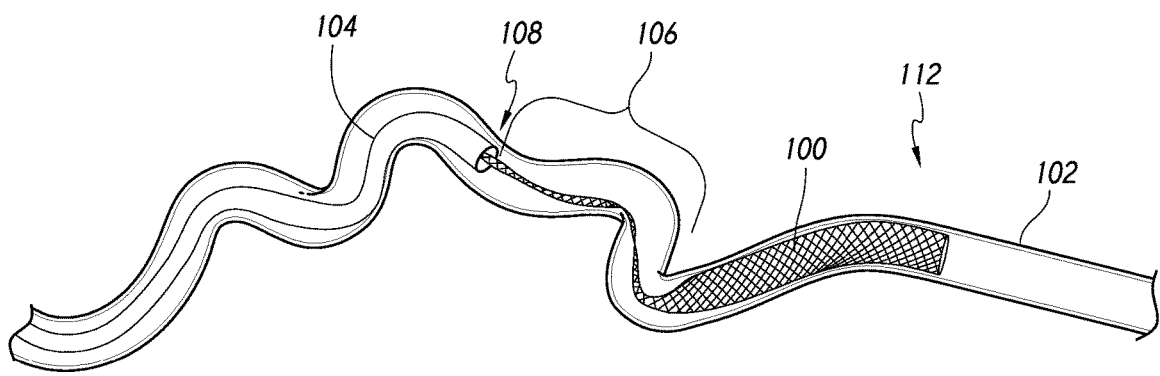
FIG. 4 illustrates deployment of a stent within the tortuous vessel of FIG. 1, the stent being kinked a location distal to the location of the kink of the stent shown in FIG. 1, and a delivery catheter retracted proximally of the kinked region of the stent.

In contrast, FIG. 4 illustrates a stent 100 that was twisted in a counterclockwise direction prior to deployment through a catheter 104 having a distal end 108 that rotated counterclockwise during retraction. As shown in FIG. 4, the stent 100 has a kinked segment 106 closer to the distal end 112 the stent than is the kinked segment 106 of FIG. 1, which illustrates deployment of a stent without any pretwist.

In some embodiments, the stent 100 can be pretwisted by at least 180° (i.e., ½ revolution), one revolution, two revolutions, three revolutions, or six revolutions. In some embodiments, the stent can be pretwisted by ½ to 10 revolutions. In some embodiments, the stent can be pretwisted by an amount that is more than necessary to collapse the stent for placement and in movement through a catheter. Other degrees of pretwisting are also contemplated. The amount of pretwisting that will allow the stent 100 to fully expand along its entire length in a tortuous vessel will depend upon the degree of virtuosity of the target vessel. A person of ordinary skill in this art having reference to the disclosure of this application can determine through routine experimentation the amount of pretwisting that sufficiently counteracts catheter rotation in particular blood vessel to allow for expansion of the stent along its entire length.

Figure 2:
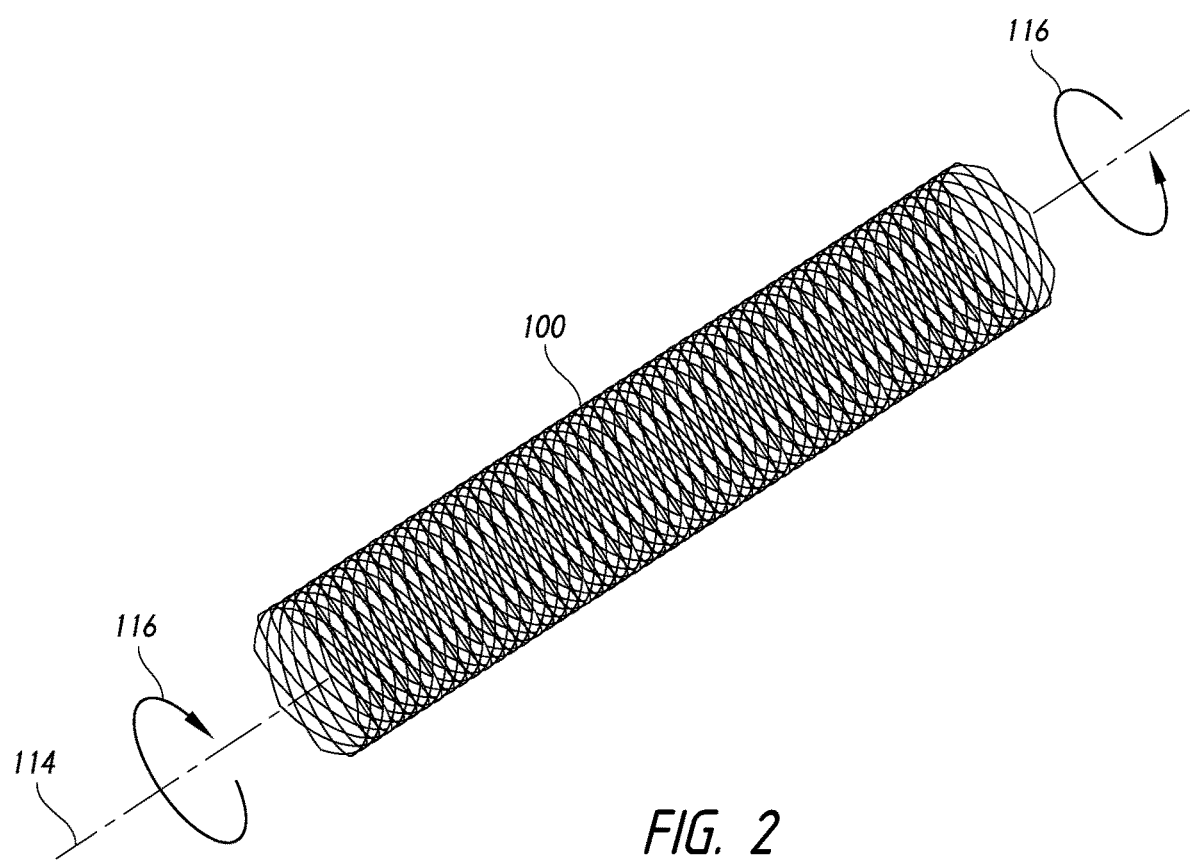
FIG. 2 illustrates twisting of a stent, according to an embodiment.

As a result of pretwisting, the stent can have one or more portions that are twisted along more than 50%, 80%, or 90% of the stent's total length, or along the stent's entire length. In some embodiments, a stent can comprise a first plurality of filaments interwoven with a second plurality of filaments, with the struts of the first and second pluralities extending helically around the longitudinal axis 114 (FIG. 2) in opposite directions prior to twisting. After twisting in some embodiments, over a twisted length of the stent, (i) both pluralities of filaments can extend helically around the longitudinal axis in the same direction with different pitches than each other, (ii) one plurality can extend helically around the longitudinal axis while the other does not, or (iii) one plurality can extend helically around the longitudinal axis with a greater pitch than it had prior to twisting, while the other plurality extends helically around the longitudinal axis with a pitch less than it had prior to twisting.

Pretwisting can be particularly advantageous for, though not limited to, long stents, such as, for example, those having a length of at least 50, 80, or 100 mm, as the distal end of the catheter travels a longer distance during deployment of the stents, and thus also applying torque to the stent over a longer distance during catheter retraction in a tortuous vessel.

In some embodiments, a braided stent can be pretwisted to a sufficient amount to reduce the braid angle and the overall stent diameter such that the stent can be pushed with less delivery force. Such amounts of pretwisting can be particularly advantageous for long stents, which require a greater force to be pushed through a catheter because of the contact area between the stent and an inner surface of the catheter. However, such benefits are not limited to long stents.

Figure 5:
FIG. 5 illustrates a twisted stent, according to an embodiment.

FIG. 5 illustrates a braided stent 100 that has been pretwisted sufficiently to reduce the braid angle and the overall stent diameter such that the stent can be pushed with less delivery force. In some embodiments, as illustrated in FIG. 5, a segment 118 of the stent can be pretwisted to have sufficient amount that the segment collapses on itself. In such embodiments, stent portions at or near one or more of the ends 110, 112 can be pretwisted to a lesser degree, including no pretwisting, such that the portion(s) self-expand against a vessel wall upon retraction of the catheter within a vessel.

Figure 8:
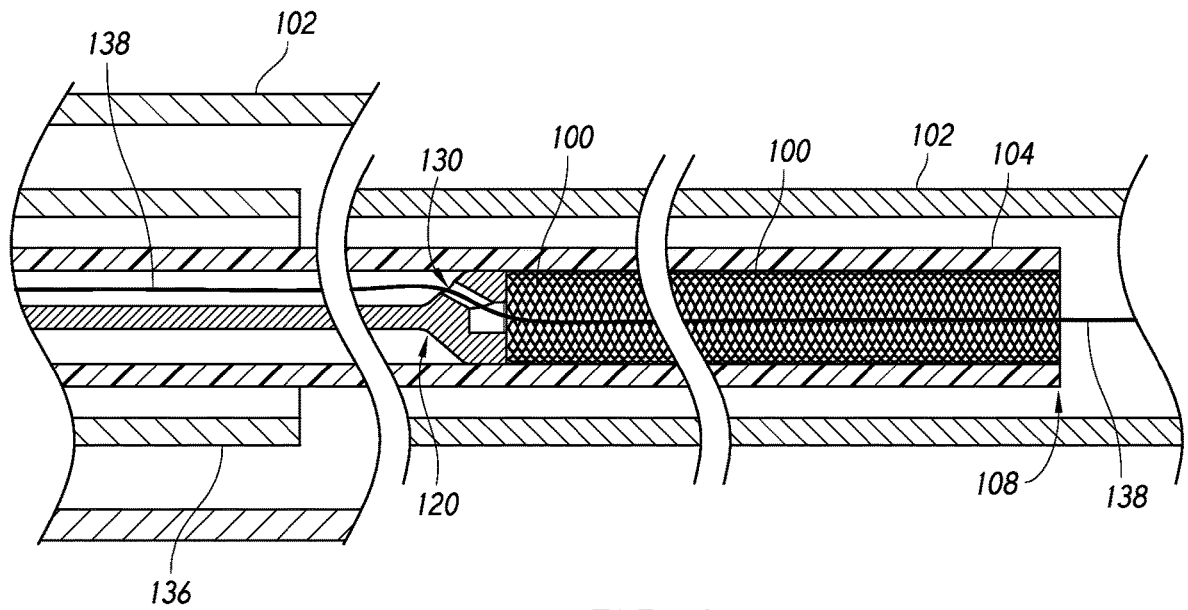
FIG. 8 schematically illustrates a guide catheter, a delivery catheter, a pusher, a guide wire, and a stent positioned within a blood vessel prior to deployment of the stent.

After being pretwisted, the stent 100 can be placed within a sheath, e.g., an introducer sheath, or catheter. In some embodiments, a pretwisted stent can be placed within a portion of a catheter near or adjacent to the distal end 108 of the catheter 104 (see, e.g., FIG. 8). In some embodiments, the stent can be retained in the distal end portion of the catheter by virtue of the stent's engagement with an inside surface of the catheter or by other features of a delivery system. In some embodiments, a pretwisted stent can be placed within a portion of a catheter near or adjacent to the proximal end (not shown) of the catheter 104, such that the stent can be advanced distally through the catheter for placement within the vessel. In any of these embodiments or others, the stent can be held in its pretwisted configuration within the sheath or catheter.

Figure 6:
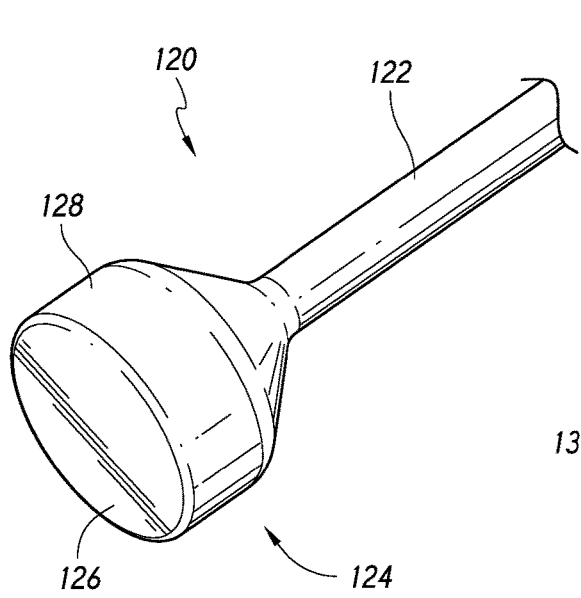
FIG. 6 is a perspective view of a distal end of a pusher, according to an embodiment.

In some embodiments, the stent 100 can be advanced through and/or out of the catheter 104 by a pusher. FIG. 6 illustrates an embodiment of a pusher 120. As illustrated in FIG. 6, the pusher 120 can comprise an elongate member 122 and a stent-engagement member 124 (also referred to simply as an engagement member).

The elongate member can have a length greater than a length of the catheter such that an operator can manipulate a proximal end of the elongate member 122 at a location proximal to a proximal end of the catheter to deploy the stent from the distal end of the catheter. The elongate member can be sufficiently flexible to allow the pusher to bend and conform to the curvature of the vasculature as needed for axial movement of the stent within the catheter and/or vasculature. The elongate member can be made of a conventional guidewire material and have a solid cross-section. Alternatively, the elongate member can be formed from a hypotube. The material used for the pusher, including the elongate member and the engagement member, can be any of the known guidewire materials including superelastic metals or shape memory alloys, e.g., nitinol, or other metals, such as, for example, stainless steel, or a combination thereof. The pusher, along any or all of its length, can comprise polytetrafluoroethylene (PTFE or TEFLON®).

In one or more embodiments, the elongate member 122 can exhibit the same degree of flexion along its entire length. In other embodiments, however, the elongate member can have two or more longitudinal sections, each with differing degrees of flexion or stiffness. The different degrees of flexion for the stent delivery system can be created using different materials and/or thicknesses within different longitudinal sections of the elongate member. In some embodiments, the flexion of the pusher can be affected by spaced cuts (not shown) formed in the elongate member. These cuts can be longitudinally and/or circumferentially spaced from each other.

The elongate member 122 and the engagement member 124 are attached. In some embodiments, the attachment between the elongate member of the engagement member can be fixed, permitting little or no relative movement between them. In some embodiments, the elongate member and the engagement member can be integrally formed, e.g., formed from a single, continuous piece of material, while in other embodiments the elongate member and the engagement member can be separately formed and subsequently attached together. In some embodiments, the elongate member and the engagement member can be rotatably attached so that the engagement member can rotate around the longitudinal axis of the engagement member.

The engagement member 124 can have a surface 126 configured to abut and push the stent 100. The distal surface 126 can be distally facing, and can be flat, for example as illustrated FIG. 6, concave, or have other shape(s). At least a portion the surface 126 is positioned to contact the stent when the stent and the pusher are within a catheter. A radially outermost part of the surface 126 is in close proximity to an inner surface of the catheter when the pusher is within the catheter such that the stent cannot extend more than slightly between the engagement member and the inner surface of the catheter. Alternatively, the radially outermost part of the surface 126 can be spaced from the inner surface of the catheter when the pusher is within the catheter such that the stent is positioned between the engagement member and the inner surface of the catheter. In such embodiments, the engagement member 124 can have an outwardly-facing surface 128 that is configured to engage the stent and, in some variants, press the stent against the inner surface of the catheter.

Although not illustrated, it is contemplated that in some embodiments the pusher can be configured to secure, grasp, or otherwise engage the stent in a manner that would permit recapture, retraction, withdrawal, or resheathing of the stent.

Figure 7A:
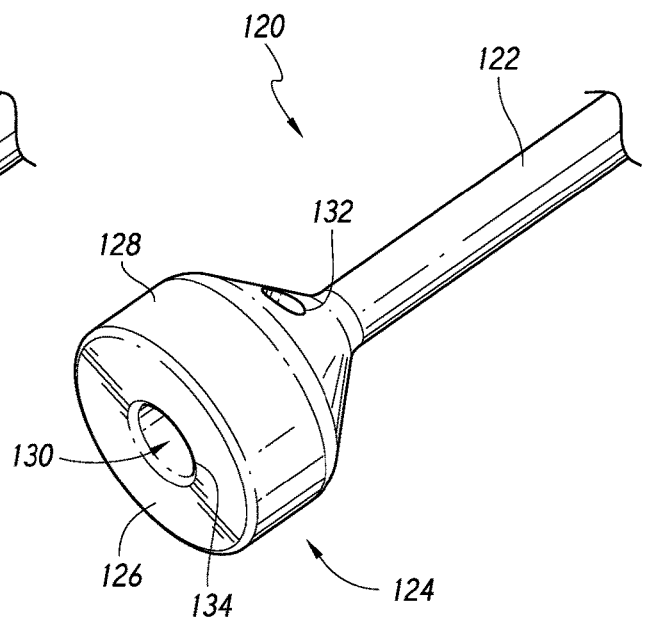
FIG. 7A is a perspective view of a distal end of a pusher comprising a lumen, according to an embodiment.
Figure 7B:
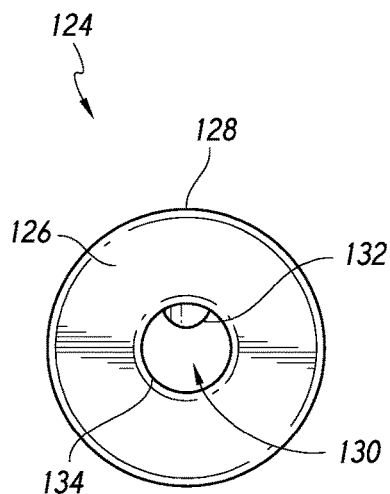
FIG. 7B is a distal end view of the pusher of FIG. 7A.
Figure 7C:
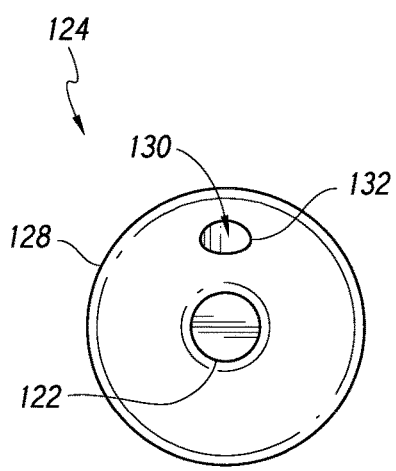
FIG. 7C is a proximal end view of the pusher of FIG. 7A.

FIGS. 7A-C illustrate an embodiment of the pusher 120 comprising an engagement member 124 having a lumen 130. The lumen 130 can have a proximal opening 132 and a proximal side of the engagement member, and a distal opening 134 on a distal side of the engagement member. The lumen, proximal opening, and distal opening can be sized to accommodate a guide wire extending therethrough.

Various methods of pretwisted stent deployment are discussed with reference to FIGS. 8-11. In some embodiments, the delivery catheter 104, which can be a microcatheter, can be advanced to a target location in a vessel 102 through a larger catheter, such as a guide catheter 136. Additionally or alternatively, the stent 100 and delivery catheter 104 can follow a guide wire 138 to the target location in the vessel. If a pusher 120 comprising a guide wire lumen, such as lumen 130, is used, the pusher can be advanced with the stent and delivery catheter over the guide wire to the target location. If the pusher lacks a guide wire lumen, the pusher can be removed from the delivery catheter or not inserted into the delivery catheter so that the stent and delivery catheter can follow the guide wire for initial positioning to the target location, and thereafter the guide wire can be removed and the pusher can be inserted.

The stent can be held in a pretwisted state until the stent is released from the catheter. In some embodiments, the stent 100 can be positioned, in a pretwisted state, in a portion of the delivery catheter 104 near or adjacent to the distal end 108 the catheter prior to insertion of the catheter into the body. The stent can then be advanced to the target location while being held in the pre-twisted state in the distal portion of the delivery catheter. In some embodiments, the stent 100 can be positioned, in a pretwisted state, in the proximal end of the delivery catheter 104 before or after the delivery catheter is advanced to the target location, and the stent can be advanced to the target location while still in a pre-twisted state.

Figure 9:
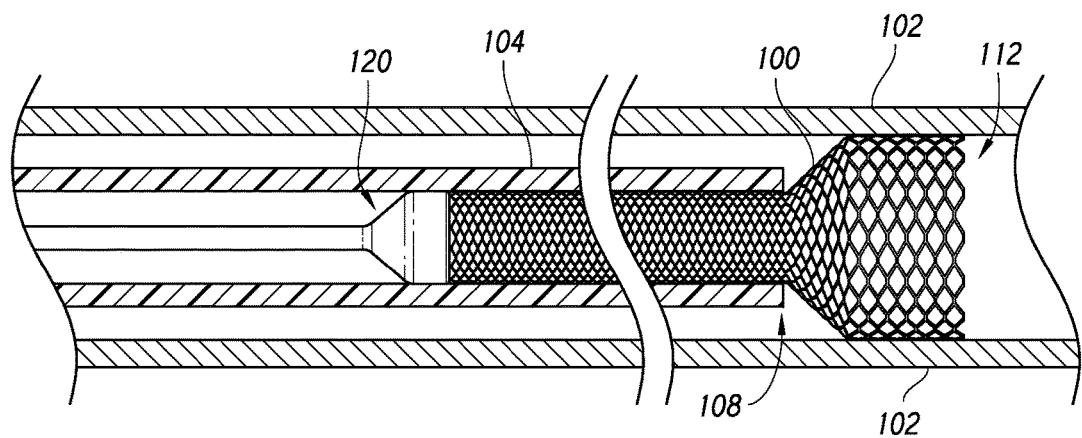
FIG. 9 schematically illustrates the delivery catheter, pusher, and stent of FIG. 8 within the blood vessel of FIG. 8 with a distal end of the stent expanded against an inner wall of the blood vessel.

After the stent 100 has been positioned at the target location in the vessel 102, the delivery catheter 104 can be retracted while maintaining or substantially maintaining a position of the pusher (that is, without intentionally moving a proximal end of the pusher) to expose a distal end 112 of the stent. If the stent is self-expanding, retraction of the catheter can allow a distal end 112 of the stent to expand into engagement with an inner wall of the vessel 102, as illustrated in FIG. 9. If the stent is not self-expanding, retraction of the catheter allows expansion of the distal end of the stent by other means, e.g., a balloon.

Positioning the stent 100 at the target location and holding the stent at the target location while retracting the delivery catheter 104 can, in some embodiments, advantageously accurately and predictably position the stent within the vessel 102 in its expanded configuration.

Figure 10:
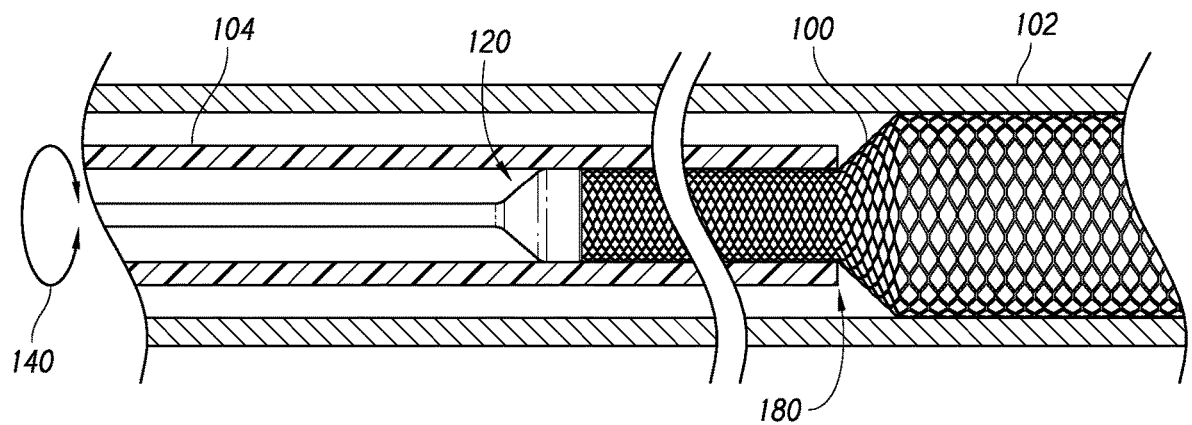
FIG. 10 schematically illustrates the delivery catheter, pusher, and stent of FIGS. 8 and 9 with the distal end of the stent expanded against the inner wall of the blood vessel, and the distal end of the delivery catheter rotating about its longitudinal axis.

Referring to FIG. 10, after the distal end 112 (FIG. 9) of the stent 100 has been expanded into engagement with the inner wall of the vessel 102, the delivery catheter 104 can be further retracted to continue exposing the stent from the distal end toward the proximal end while the distal end 108 of the delivery catheter is rotated as indicated by arrow 140. The distal end 108 can rotate by virtue of the tortuous curvature of the vessel 102 traversed during retraction of the delivery catheter 104 while the proximal end of the delivery catheter is prevented from rotating, not intentionally rotated, or rotated less than 90° or 180°, for example.

During retraction of the delivery catheter 104, the pusher 120 can be maintained or substantially maintained in its position, advanced, or retracted, depending upon various factors, which may include the desired porosity on full expansion, the ratio of the collapsed stent diameter to the expanded stent diameter, and anatomical features adjacent the stent, e.g., aneurysms and branch vessels.

Figure 11:
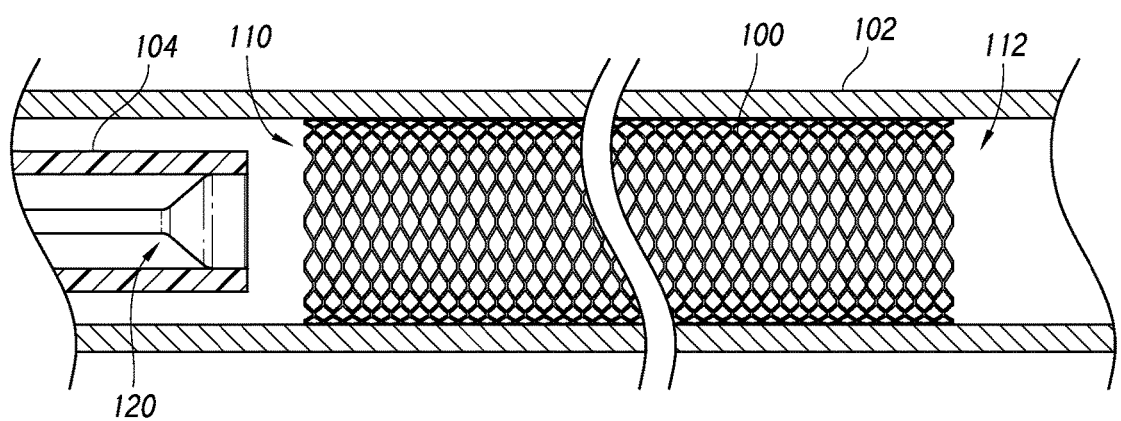
FIG. 11 schematically illustrates the delivery catheter, pusher, and stent of FIGS. 8-10, and the entire length of the stent expanded against the inner wall of the blood vessel without a kink.

As illustrated in FIG. 11, the delivery catheter 104 can be retracted to allow the proximal end 110 of the stent to expand into engagement with the inner surface of the vessel 102. In some embodiments, the distal end 108 of the delivery catheter 104 can rotate at least 180° (i.e., ½ revolution), one revolution, two revolutions, three revolutions, or six revolutions during retraction of the delivery catheter to fully expose the stent 100. In some embodiments, the distal end 108 can rotate by ½ to 10 revolutions during retraction of the delivery catheter to fully expose the stent 100. The distal end 108 can rotate to a greater, equal, or lesser amount than the pretwist of the stent 100. However, in at least some embodiments, the amount of rotation of the distal end 108 and the amount of pretwist are close enough that the stent fully expands against the inner wall of the vessel 102 along its entire length without repeated advancement and retraction of the delivery catheter 104. In some embodiments, the amount of rotation of the distal end 108 and the amount of pretwisted are close enough that, without repeated advancement and retraction of the delivery catheter 104, a majority (greater than 50%) of the stent expands against the inner wall of the vessel 102, and no portion of the stent expands less than 50% of the vessel diameter at that location.

Although FIGS. 9-11 do not show the guide wire 138, the methods disclosed herein can optionally be performed with a guide wire or other elongate member, such as, for example, a core wire or support wire, extending through the stent in 100 during expansion within the vessel 102.

Although methods for preparing a stent for placement in a vessel and for expanding a stent within a vessel have been described with reference to a delivery catheter, in some embodiments, a sheath can be employed in each of the uses for which a delivery catheter has been mentioned.

Information regarding additional embodiments of the stent delivery systems and additional details and components that can optionally be used or implemented in embodiments of the subject technology are provided in the above-incorporated U.S. patents, patent applications, and patent application publications.

Some blood vessels have mirrored configurations across a medial plane of the body. For example, intracranial arteries on the right side of the body and on the left side of the body are near mirror images of each other. Thus, a distal end of a catheter will rotate in opposite directions through corresponding intravascular paths on opposing sides of a brain. Therefore, for example, a stent pretwisted for placement in the middle cerebral artery on the left side of the brain can have an opposite direction of pretwist from a stent pretwisted for placement in the middle cerebral artery on the right side of the brain.

Figure 12:
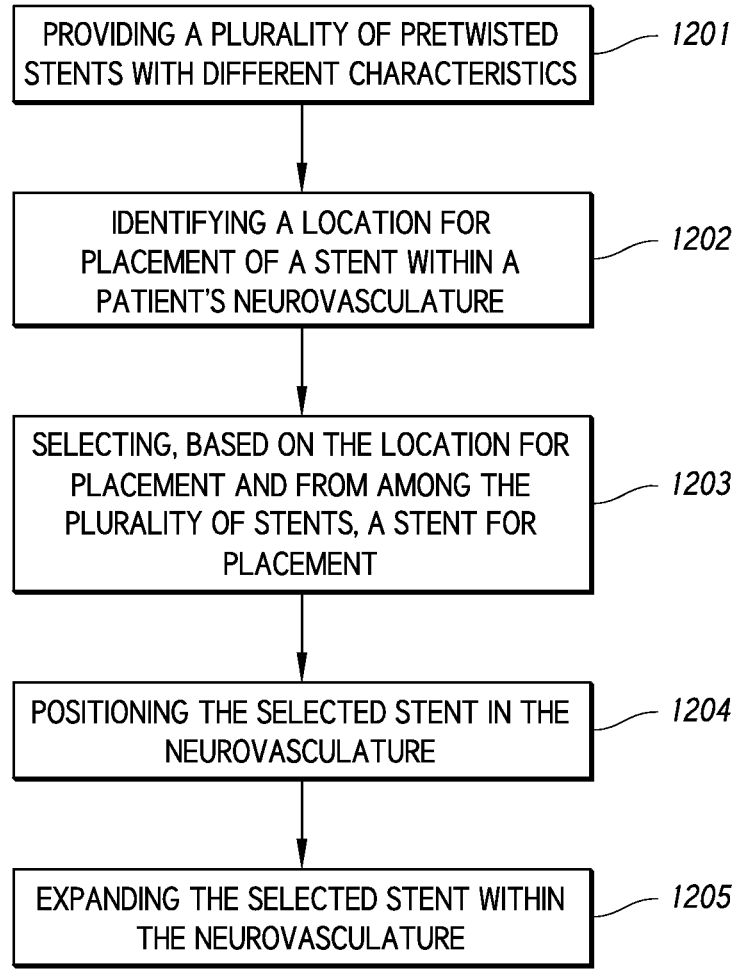
FIG. 12 is flow chart of a method of selecting and placing a stent, according to an embodiment.

In some embodiments, a system of stents can comprise a plurality of stents configured for placement at various intravascular locations. The stents can have various sizes, lengths, directions of pretwist, and amounts of pretwist that depend, at least in part, on the target vessel for placement, and on which side of the brain the target vessel is located. Methods for selecting appropriate stent for placement in a patient and placing the stent in the patient are described with reference to FIG. 12. As indicated at box 1201, a plurality of stents such as just described can be provided. As indicated at box 1202, in some embodiments, a target vessel for placement of a stent can be identified, such as, for example, by appropriate imaging procedure, e.g., magnetic resonance imaging or computed tomography. As indicated at box 1203, a stent for placement can be selected from the plurality based, at least in part, on the target location for placement. The selection can comprise selecting between a clockwise pretwisted stent and a counterclockwise pretwisted stent based on which side of the patient's body the target location resides. As indicated at box 1204, the selected stent can then be positioned within the patient's body of the target location, for example, by the methods disclosed herein. As indicated at box 1205, the selected stent can then be expanded within at the target location, for example, by the methods disclosed herein.

The apparatus and methods discussed herein are not limited to the expansion and use of a stent within any particular vessels, but may include any number of different types of vessels. For example, in some aspects, vessels may include arteries or veins. The vessels may have bifurcations and/or sharp turns. In some aspects, the vessels may be suprathoracic vessels (e.g., vessels in the neck or above), intrathoracic vessels (e.g., vessels in the thorax), subthoracic vessels (e.g., vessels in the abdominal area or below), lateral thoracic vessels (e.g., vessels to the sides of the thorax such as vessels in the shoulder area and beyond), or other types of vessels and/or branches thereof.

In some aspects, the suprathoracic vessels may comprise at least one of intracranial vessels, cerebral arteries, and/or any branches thereof. For example, the suprathoracic vessels may comprise at least one of a common carotid artery, an internal carotid artery, an external carotid artery, a middle meningeal artery, superficial temporal arteries, an occipital artery, a lacrimal (ophthalmic) artery, an accessory meningeal artery, an anterior ethmoidal artery, a posterior ethmoidal artery, a maxillary artery, a posterior auricular artery, an ascending pharyngeal artery, a vertebral artery, a left middle meningeal artery, a posterior cerebral artery, a superior cerebellar artery, a basilar artery, a left internal acoustic (labyrinthine) artery, an anterior inferior cerebellar artery, a left ascending pharyngeal artery, a posterior inferior cerebellar artery, a deep cervical artery, a highest intercostal artery, a costocervical trunk, a subclavian artery, a middle cerebral artery, an anterior cerebral artery, an anterior communicating artery, an ophthalmic artery, a posterior communicating artery, a facial artery, a lingual artery, a superior laryngeal artery, a superior thyroid artery, an ascending cervical artery, an inferior thyroid artery, a thyrocervical trunk, an internal thoracic artery, and/or any branches thereof. The suprathoracic vessels may also comprise at least one of a medial orbitofrontal artery, a recurrent artery (of Heubner), medial and lateral lenticulostriate arteries, a lateral orbitofrontal artery, an ascending frontal (candelabra) artery, an anterior choroidal artery, pontine arteries, an internal acoustic (labyrinthine) artery, an anterior spinal artery, a posterior spinal artery, a posterior medial choroidal artery, a posterior lateral choroidal artery, and/or branches thereof. The suprathoracic vessels may also comprise at least one of perforating arteries, a hypothalamic artery, lenticulostriate arteries, a superior hypophyseal artery, an inferior hypophyseal artery, an anterior thalamostriate artery, a posterior thalamostriate artery, and/or branches thereof. The suprathoracic vessels may also comprise at least one of a precentral (pre-Rolandic) and central (Rolandic) arteries, anterior and posterior parietal arteries, an angular artery, temporal arteries (anterior, middle and posterior), a paracentral artery, a pericallosal artery, a callosomarginal artery, a frontopolar artery, a precuneal artery, a parietooccipital artery, a calcarine artery, an inferior vermian artery, and/or branches thereof.

In some aspects, the suprathoracic vessels may also comprise at least one of diploic veins, an emissary vein, a cerebral vein, a middle meningeal vein, superficial temporal veins, a frontal diploic vein, an anterior temporal diploic vein, a parietal emissary vein, a posterior temporal diploic vein, an occipital emissary vein, an occipital diploic vein, a mastoid emissary vein, a superior cerebral vein, efferent hypophyseal veins, infundibulum (pituitary stalk) and long hypophyseal portal veins, and/or branches thereof.

The intrathoracic vessels may comprise the aorta or branches thereof. For example, the intrathoracic vessels may comprise at least one of an ascending aorta, a descending aorta, an arch of the aorta, and/or branches thereof. The descending aorta may comprise at least one of a thoracic aorta, an abdominal aorta, and/or any branches thereof. The intrathoracic vessels may also comprise at least one of a subclavian artery, an internal thoracic artery, a pericardiacophrenic artery, a right pulmonary artery, a right coronary artery, a brachiocephalic trunk, a pulmonary trunk, a left pulmonary artery, an anterior interventricular artery, and/or branches thereof. The intrathoracic vessels may also comprise at least one of an inferior thyroid artery, a thyrocervical trunk, a vertebral artery, a right bronchial artery, a superior left bronchial artery, an inferior left bronchial artery, aortic esophageal arteries, and/or branches thereof In some aspects, the intrathoracic vessels may also comprise at least one of a right internal jugular vein, a right brachiocephalic vein, a subclavian vein, an internal thoracic vein, a pericardiacophrenic vein, a superior vena cava, a right superior pulmonary vein, a left brachiocephalic vein, a left internal jugular vein, a left superior pulmonary vein, an inferior thyroid vein, an external jugular vein, a vertebral vein, a right highest intercostal vein, a 6th right intercostal vein, an azygos vein, an inferior vena cava, a left highest intercostal vein, an accessory hemiazygos vein, a hemiazygos vein, and/or branches thereof.

In some aspects, the subthoracic vessels may comprise at least one of renal arteries, inferior phrenic arteries, a celiac trunk with common hepatic, left gastric and splenic arteries, superior suprarenal arteries, a middle suprarenal artery, an inferior suprarenal artery, a right renal artery, a subcostal artery, 1st to 4th right lumbar arteries, common iliac arteries, an iliolumbar artery, an internal iliac artery, lateral sacral arteries, an external iliac artery, a testicular (ovarian) artery, an ascending branch of deep circumclex iliac artery, a superficial circumflex iliac artery, an inferior epigastric artery, a superficial epigastric artery, a femoral artery, a ductus deferens and testicular artery, a superficial external pudendal artery, a deep external pudendal artery, and/or branches thereof. The subthoracic vessels may also comprise at least one of a superior mesenteric artery, a left renal artery, an abdominal aorta, an inferior mesenteric artery, colic arteries, sigmoid arteries, a superior rectal artery, 5th lumbar arteries, a middle sacral artery, a superior gluteal artery, umbilical and superior vesical arteries, an obturator artery, an inferior vesical and artery to ductus deferens, a middle rectal artery, an internal pudendal artery, an inferior gluteal artery, a cremasteric, pubic (obturator anastomotic) branches of inferior epigastric artery, a left colic artery, rectal arteries, and/or branches thereof.

In some aspects, the lateral thoracic vessels may comprise at least one of humeral arteries, a transverse cervical artery, a suprascapular artery, a dorsal scapular artery, and/or branches thereof. The lateral thoracic vessels may also comprise at least one of an anterior circumflex humeral artery, a posterior circumflex humeral artery, a subscapular artery, a circumflex scapular artery, a brachial artery, a thoracodorsal artery, a lateral thoracic artery, an inferior thyroid artery, a thyrocervical trunk, a subclavian artery, a superior thoracic artery, a thoracoacromial artery, and/or branches thereof.

In some embodiments, the stent 100 can be configured to be placed across an aneurysm. The occluding device can be delivered through the distal portion of the catheter and into the vasculature adjacent an aneurysm in, for example, the middle cerebral artery. A proximal portion of the delivery catheter can remain partially or entirely within a guiding catheter during delivery, and an intermediate portion, taper portion, and distal portion of the delivery catheter can extend distally of a guide catheter, if present. The stent can be released at the target location and can be used to occlude blood flow into the aneurysm. The delivery catheter can be used to reach target locations (e.g., aneurysms) located elsewhere in the body as well, include but not limited to other arteries, branches, and blood vessels such as those described above.

The apparatus and methods discussed herein are not limited to the deployment and use of a stent within the vascular system but may include any number of further treatment applications. Other treatment sites may include areas or regions of the body such as organ bodies.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A stent assembly comprising:
 a stent having a first end, a second end, and a tubular, mesh wall between the first end and the second end, the mesh wall being contiguous in circumferential and longitudinal directions from the first end to the second end, the stent having an untwisted rest configuration in the absence of external forces, and a twisted configuration in which the stent is twisted about the longitudinal axis from the rest configuration to a sufficient amount that a segment of the stent between the first and second ends collapses upon itself, forming a constriction,
 a sheath, wherein the stent is held in the sheath in the twisted configuration; and
 a pusher having an elongate member at least partially disposed within the sheath and a stent-engagement member configured to abut and engage the stent.

2. The stent assembly of claim 1, wherein, in the twisted configuration, the first end of the stent is rotated, about the longitudinal axis, relative to the second end more than is necessary to collapse the stent for positioning the stent in the sheath.

3. The stent assembly of claim 1, wherein the stent has a length of at least 50 mm.

4. The stent assembly of claim 1, wherein the stent comprises a plurality of braided filaments.

5. The stent assembly of claim 1, wherein, in the twisted configuration, the first end of the stent is rotated, about the longitudinal axis, by at least 180 degrees relative to the second end of the stent in the rest configuration.

6. The stent assembly of claim 5, wherein, in the twisted configuration, the first end of the stent is rotated, about the longitudinal axis, by at least 360 degrees relative to the second end of the stent in the rest configuration.

7. A kit comprising: a plurality of stents, each stent comprising a first end, a second end, and a tubular, mesh wall between the first end and the second end, the mesh wall being contiguous in circumferential and longitudinal directions from the first end to the second end, each stent having an untwisted rest configuration in the absence of external forces, and a twisted configuration in which each stent is twisted about the longitudinal axis from the rest configuration to a sufficient amount that a segment of each stent between the first and second ends collapses upon itself, forming a constriction;
wherein a first stent of the plurality of stents is in the twisted configuration, and is twisted in a first rotational direction about the longitudinal axis from its rest configuration, wherein the first stent is held in the twisted first rotational direction by a first sheath; a pusher having an elongate member at least partially disposed within the first sheath proximal to the first stent and a stent-engagement surface configured to abut and engage the first stent; and wherein a second stent of the plurality of stents is in the twisted configuration, and is twisted in a second rotational direction, opposite the first rotational direction, about the longitudinal axis from its rest configuration, wherein the second stent is held in the twisted second rotational direction by a second sheath.

8. The kit of claim 7, wherein, in the twisted configuration, the first end is rotated, about the longitudinal axis, by at least 180 degrees relative to the second end in the rest configuration.

9. The kit of claim 7, wherein, in the twisted configuration, the first end is rotated, about the longitudinal axis, by at least 360 degrees relative to the second end in the rest configuration.

10. The kit of claim 7, wherein at least one stent of the plurality of stents is in the twisted configuration and its first end is twisted by at least 720 degrees relative to its second end in the rest configuration, and at least another stent of the plurality of stents is in the twisted configuration and its first end is twisted by less than 720 degrees relative to its second end in the rest configuration.

11. The kit of claim 7, wherein, in the twisted configuration, the first end of the first stent is rotated, about the longitudinal axis, relative to the second end of the first stent more than is necessary to collapse the first stent for positioning the first stent in the first sheath.

12. The kit of claim 7, wherein at least one of the plurality of stents has a length of 50 mm to 70 mm, and another of the plurality of stents has a length of greater than 70 mm.

13. The kit of claim 7, wherein each stent of the plurality of stents comprises a plurality of braided filaments.

14. The kit of claim 7, wherein the first end of each stent is expanded against an inner wall of its corresponding sheath.

15. The kit of claim 14, wherein the second end of each stent is expanded against the inner wall of its corresponding sheath.

* * * * *